(12) United States Patent
Pless

(10) Patent No.: US 8,694,106 B2
(45) Date of Patent: Apr. 8, 2014

(54) NEUROSTIMULATOR INVOLVING STIMULATION STRATEGIES AND PROCESS FOR USING IT

(71) Applicant: NeuroPace, Inc., Mountain View, CA (US)

(72) Inventor: Benjamin D. Pless, Atherton, CA (US)

(73) Assignee: NeuroPace, Inc., Mountain View, CA (US)

( * ) Notice: Subject to any disclaimer, the term of this patent is extended or adjusted under 35 U.S.C. 154(b) by 0 days.

(21) Appl. No.: 13/781,186

(22) Filed: Feb. 28, 2013

(65) Prior Publication Data

US 2013/0178914 A1 Jul. 11, 2013

Related U.S. Application Data

(62) Division of application No. 13/106,747, filed on May 12, 2011, now Pat. No. 8,412,333, which is a division of application No. 11/142,063, filed on May 31, 2005, now Pat. No. 8,073,544, which is a division of application No. 09/543,264, filed on Apr. 5, 2000, now Pat. No. 6,944,501.

(51) Int. Cl.
*A61N 1/00* (2006.01)
*A61B 5/04* (2006.01)

(52) U.S. Cl.
USPC .............................. 607/45; 607/62; 600/544

(58) Field of Classification Search
USPC ...................................... 607/45, 62; 600/544
See application file for complete search history.

(56) References Cited

U.S. PATENT DOCUMENTS

| | | | |
|---|---|---|---|
| 3,531,561 A | 9/1970 | Trehu |
| 3,565,066 A | 2/1971 | Roaf et al. |
| 3,636,956 A | 1/1972 | Schneider |
| 3,960,151 A | 6/1976 | Kuhn |
| 3,993,046 A | 11/1976 | Fernandez et al. |
| 4,429,690 A | 2/1984 | Angelino-Pievani |
| 4,523,591 A | 6/1985 | Kaplan et al. |
| 4,566,464 A | 1/1986 | Piccone et al. |
| 4,702,254 A | 10/1987 | Zabara |
| 4,753,246 A | 6/1988 | Freeman |
| 4,781,183 A | 11/1988 | Casey et al. |
| 4,833,403 A | 5/1989 | Tamamura et al. |
| 4,867,164 A | 9/1989 | Zabara |
| 4,873,981 A | 10/1989 | Abrams et al. |

(Continued)

FOREIGN PATENT DOCUMENTS

| | | |
|---|---|---|
| DE | 8528003 | 2/1986 |
| DE | 8706912 | 10/1987 |

(Continued)

OTHER PUBLICATIONS

Andriano, K.P. et al., "Processing and Characterization of Absorbable Polyactide Polymers for Use in Surgical Implants", Journal of Applied Biomaterials. 5, (1994),133-140.

(Continued)

*Primary Examiner* — Nicole F Lavert
(74) *Attorney, Agent, or Firm* — Arent Fox LLP

(57) ABSTRACT

This is a neurostimulator that is configured to treat epilepsy and other neurological disorders using certain stimulation strategies, particularly changing various pulse parameters, during the imposition of a burst of those pulses. The invention includes the processes embodying those stimulation strategies.

20 Claims, 8 Drawing Sheets

(56) References Cited

U.S. PATENT DOCUMENTS

| | | |
|---|---|---|
| 4,905,680 A | 3/1990 | Tunc |
| 4,979,511 A | 12/1990 | Terry |
| 5,025,807 A | 6/1991 | Zabara |
| 5,031,618 A | 7/1991 | Mullett |
| 5,129,903 A | 7/1992 | Luhr et al. |
| 5,154,172 A | 10/1992 | Terry et al. |
| 5,179,950 A | 1/1993 | Stanislaw |
| 5,186,170 A | 2/1993 | Varrichio et al. |
| 5,188,104 A | 2/1993 | Wernicke et al. |
| 5,205,285 A | 4/1993 | Baker |
| 5,215,086 A | 6/1993 | Terry et al. |
| 5,215,089 A | 6/1993 | Baker |
| 5,222,494 A | 6/1993 | Baker |
| 5,231,988 A | 8/1993 | Wernicke et al. |
| 5,235,980 A | 8/1993 | Varrichio et al. |
| 5,237,991 A | 8/1993 | Baker et al. |
| 5,251,634 A | 10/1993 | Weinberg |
| 5,263,480 A | 11/1993 | Wernicke et al. |
| 5,269,303 A | 12/1993 | Wernicke et al. |
| 5,293,879 A | 3/1994 | Vonk et al. |
| 5,299,569 A | 4/1994 | Wernicke et al. |
| 5,304,206 A | 4/1994 | Baker et al. |
| 5,311,876 A | 5/1994 | Olsen et al. |
| 5,330,515 A | 7/1994 | Rutecki et al. |
| 5,335,657 A | 8/1994 | Terry et al. |
| 5,349,962 A | 9/1994 | Lockard et al. |
| 5,351,394 A | 10/1994 | Weinberg |
| 5,372,598 A | 12/1994 | Luhr et al. |
| 5,413,577 A | 5/1995 | Pollock |
| 5,474,547 A | 12/1995 | Aebischer et al. |
| 5,522,863 A | 6/1996 | Spano et al. |
| 5,531,778 A | 7/1996 | Maschino et al. |
| 5,540,730 A | 7/1996 | Terry et al. |
| 5,540,734 A | 7/1996 | Zabara |
| 5,569,250 A | 10/1996 | Sarver et al. |
| 5,571,150 A | 11/1996 | Wernicke et al. |
| 5,604,204 A | 2/1997 | Ammann et al. |
| 5,676,655 A | 10/1997 | Howard et al. |
| 5,683,422 A | 11/1997 | Rise |
| 5,707,396 A | 1/1998 | Benabid |
| 5,707,400 A | 1/1998 | Terry et al. |
| 5,711,316 A | 1/1998 | Elsberry et al. |
| 5,713,923 A | 2/1998 | Ward et al. |
| 5,716,377 A | 2/1998 | Rise et al. |
| 5,735,814 A | 4/1998 | Elsberry et al. |
| 5,752,979 A | 5/1998 | Benabid |
| 5,792,186 A | 8/1998 | Rise |
| 5,792,212 A | 8/1998 | Weijand |
| 5,800,459 A | 9/1998 | Spano et al. |
| 5,800,474 A | 9/1998 | Benabid et al. |
| 5,832,932 A | 11/1998 | Elsberry et al. |
| 5,833,709 A | 11/1998 | Rise et al. |
| 5,868,746 A | 2/1999 | Sarver et al. |
| 5,871,506 A | 2/1999 | Mower |
| 5,895,416 A | 4/1999 | Barreras et al. |
| 5,916,239 A | 6/1999 | Geddes et al. |
| 5,928,272 A | 7/1999 | Adkins et al. |
| 5,938,689 A | 8/1999 | Fischell et al. |
| 5,978,702 A | 11/1999 | Ward et al. |
| 5,983,141 A * | 11/1999 | Sluijter et al. .................. 607/100 |
| 6,006,124 A | 12/1999 | Fischell et al. |
| 6,016,449 A | 1/2000 | Fischell et al. |
| 6,018,682 A | 1/2000 | Rise |
| 6,024,702 A | 2/2000 | Iversen |
| 6,061,593 A | 5/2000 | Fischell et al. |
| 6,095,148 A | 8/2000 | Shastri et al. |
| 6,128,538 A | 10/2000 | Fischell et al. |
| 6,134,806 A | 10/2000 | Dhaemers |
| 6,161,045 A | 12/2000 | Fischell et al. |
| 6,230,049 B1 | 5/2001 | Fischell et al. |
| 6,263,237 B1 | 7/2001 | Rise |
| 6,354,299 B1 | 3/2002 | Fischell et al. |
| 6,356,777 B1 | 3/2002 | Garfield et al. |
| 6,360,122 B1 | 3/2002 | Fischell et al. |
| 6,366,813 B1 | 4/2002 | DiLorenzo et al. |
| 6,427,086 B1 | 7/2002 | Fischell et al. |
| 6,463,328 B1 | 10/2002 | John |
| 6,466,822 B1 | 10/2002 | Pless |
| 6,480,743 B1 | 11/2002 | Kirkpatrick et al. |
| 6,597,954 B1 | 7/2003 | Pless et al. |
| 6,690,974 B2 | 2/2004 | Archer et al. |
| 6,819,956 B2 | 11/2004 | DiLorenzo |
| 6,944,501 B1 | 9/2005 | Pless |
| 7,174,213 B2 | 2/2007 | Pless |
| 7,209,787 B2 | 4/2007 | DiLorenzo |
| 7,231,254 B2 | 6/2007 | DiLorenzo |
| 7,242,984 B2 | 7/2007 | DiLorenzo |
| 7,277,758 B2 | 10/2007 | DiLorenzo |
| 7,324,851 B1 | 1/2008 | DiLorenzo |
| 7,403,820 B2 | 7/2008 | DiLorenzo |
| 7,853,329 B2 | 12/2010 | DiLorenzo |
| 2002/0077670 A1 | 6/2002 | Archer et al. |
| 2007/0161919 A1 | 7/2007 | DiLorenzo |

FOREIGN PATENT DOCUMENTS

| | | |
|---|---|---|
| DE | 3701765 | 6/1988 |
| DE | 4028021 | 5/1991 |
| EP | 0195455 A1 | 9/1986 |
| EP | 0276153 A2 | 7/1988 |
| EP | 0290138 A2 | 11/1988 |
| EP | 0291632 A1 | 11/1988 |
| EP | 0290138 A3 | 1/1989 |
| EP | 0276153 A3 | 9/1989 |
| EP | 0347658 A1 | 12/1989 |
| EP | 0195455 B1 | 2/1990 |
| EP | 0491983 A1 | 7/1992 |
| EP | 0291632 B1 | 7/1993 |
| EP | 0347658 B1 | 9/1993 |
| EP | 0433852 | 3/1996 |
| EP | 0491983 B1 | 3/1996 |
| EP | 0290138 B1 | 7/1996 |
| EP | 0291632 B2 | 8/1998 |
| EP | 0911061 A2 | 4/1999 |
| EP | 0911061 A3 | 11/1999 |
| EP | 0911061 B1 | 10/2005 |
| GB | 2140523 | 11/1984 |

OTHER PUBLICATIONS

Chkhenkeli, S.A. and, Chkhenkeli, I.S. et al., (1997). "Effects of Therapeutic Stimulation of Nucleus Caudatus on Epileptic Electrical Activity of Brain in Patents with Intractable Epilepsy," Stereotact Funct Neurosurg 69:221-224.

Cooper, I.S. et al., "The Effect of Chronic Stimulation of Cerebellar Cortex on Epilepsy in Man", In the Cerebellum, Epilepsy, and Behavior. Pleman Press:New York, (1974),119-171.

Cooper, I.S. et al., "Saftey and Efficacy of Chronic Cerebellar Stimulation", Appl. Neurophysiol. 40, (1977/78),124-134.

Cooper, I.S. et al., "Effects of Cerebellar Stimulation on Epilepsy, the EEG and Cerebral Palsy in Man", *In Contemporary Clinical Neurophysiology* (*EEG Suppl.* No. 34). Cobb, W.A. et al., eds., *Elsevier Scientific Publishing*: Amsterdam, (1978),349-354.

Davis, R. et al., "Cerebellar Stimulation for Seizure Control: 17-Year Study", Stereotact. Funct. Neurosurg. 58, (1992),200-208.

Eppley, B.L. et al., "Effects of Resorbable Fixation on Craniofacial Skeletal Growth: A Pilot Experimental Study", Journal of Craniofacial Surgery 3(4), (1992),190-196.

Gerlach, K.L. "In-vivo and Clinical Evaluations of Poly(L-lactide) Plates and Screws for Use in Maxillofacial Traumatology", Clinical Materials. 13, (1993),21-28.

Gotman, J. "Automatic Detection of Seizures and Spikes", Journal of Clinical Neurophysiology. 16(2), (1999),130-140.

Osario, I. et al., "A Method for Accurate Automated Real-Time Seizure Detection", Epilepsia, 36(supplement 4), (1995),4.

Qu, H. et al., "A Seizure Warning System for Long-Term Epilepsy Monitoring", Neurology. 45, (1995),2250-2254.

Sayler, K.E. et al., "A Comparative Study of the Effects of Biodegradable and Titanium Plating Systems on Cranial Growth and Structure: Experimental Study in Beagles", Plastic and Reconstructive Surgery 93(4), (1994),705-713.

(56) References Cited

OTHER PUBLICATIONS

Schiff, S. et al., "Controlling Chaos in the Brain", Nature. 370, (1994),615-620.
Thaller, S.R. et al., "Use of Biodegradable Plates and Screws in a Rabbit Model", Journal of Craniofacial Surgery 2(4), (1992),168-173.
Velasco, F. et al., "Electrical Stimulation of the Centromedian Thalamic Nucleus in Control of Seizures: Long Term Studies", Epilepsia. 36(1), (1995),63-71.
U.S. Appl. No. 60/095,413, filed Aug. 5, 1998.
Communication Dated Mar. 1, 2004 European Search Report for counterpart foreign application EP Patent Application No. 01303246., (Mar. 1, 2004),1.
Communication pursuant to Article 96(2) EPC dated Oct. 18, 2005 for counterpart foreign application EP Patent Application No. 01303246., (Oct. 18, 2005),1.
Applicant Response dated Apr. 13, 2006 to Communication pursuant to Article 96(2) EPC dated Oct. 18, 2005 for counterpart foreign application EP Patent Application No. 01303246., (Apr. 13, 2006),1.
Communication pursuant to Article 96(2) EPC dated Mar. 9, 2007 for counterpart foreign application EP Patent Application No. 01303246., (Mar. 9, 2007),1.
Communication Dated Mar. 8, 2004 European Search Report for counterpart foreign application EP Patent Application No. 01303245., (Mar. 8, 2004),3.
Communication pursuant to Article 96(2) EPC dated Oct. 14, 2005 for counterpart foreign application EP Patent Application No. 01303245., (Oct. 14, 2005),3.
Applicant Response dated Apr. 20, 2006 to Communication pursuant to Article 96(2) EPC dated Oct. 14, 2005 for counterpart foreign application EP Patent Application No. 01303245., (Apr. 20, 2006),3.
Communication pursuant to Article 96(2) EPC dated Mar. 9, 2007 for counterpart foreign application EP Patent Application No. 01303245., (Mar. 9, 2007),3.
U.S. Appl. No. 13/106,729 Office action mailed Jul. 25, 2011.
U.S. Appl. No. 13/106,729 Office action mailed Nov. 14, 2011.
U.S. Appl. No. 13/106,729 Office action mailed Apr. 25, 2012.
U.S. Appl. No. 60/562,487, filed Apr. 14, 2004.
U.S. Appl. No. 60/460,140, filed Apr. 3, 2003.
U.S. Appl. No. 60/438,286, filed Jan. 6, 2003.
U.S. Appl. No. 60/427,699, filed Nov. 20, 2002.
U.S. Appl. No. 60/436,792, filed Dec. 27, 2002.

* cited by examiner

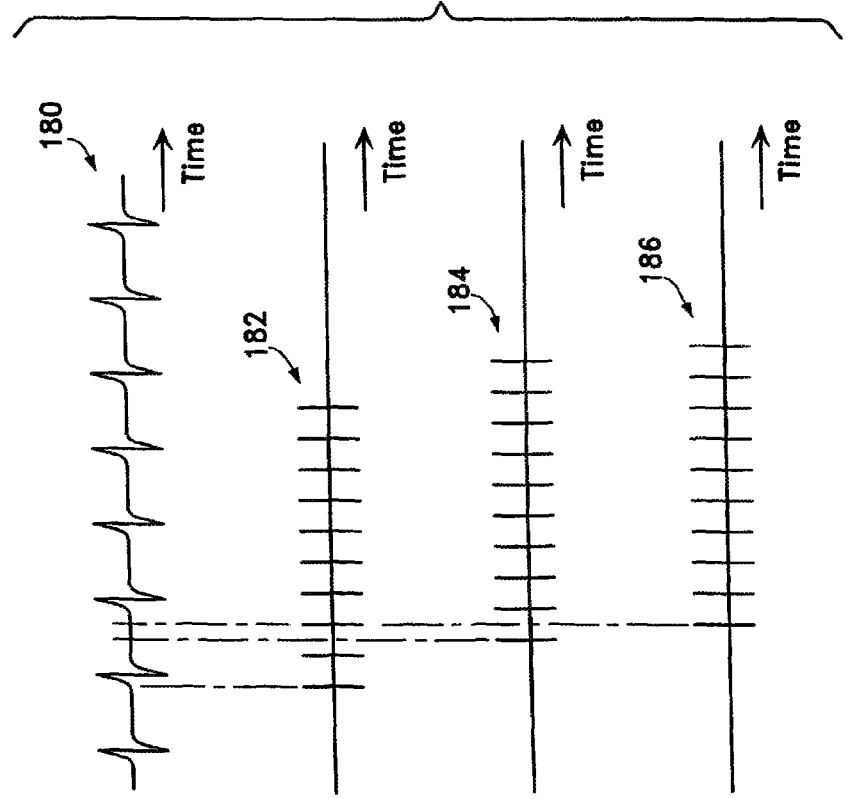

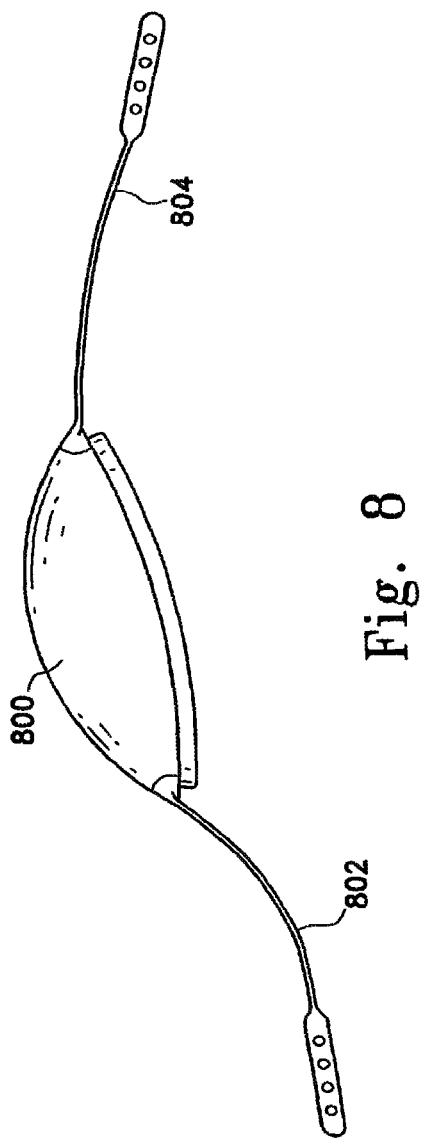

NEUROSTIMULATOR INVOLVING STIMULATION STRATEGIES AND PROCESS FOR USING IT

CROSS-REFERENCE TO RELATED APPLICATIONS

This application is a divisional application of and claims the benefit of co-pending U.S. patent application Ser. No. 13/106,747 filed on May 12, 2011 entitled "NEUROSTIMULATOR INVOLVING STIMULATION STRATEGIES AND PROCESS FOR USING IT" by Benjamin D. Pless, which is a divisional of U.S. patent application Ser. No. 11/142,063 filed May 31, 2005, now U.S. Pat. No. 8,073,544, issued Dec. 6, 2011, which is a divisional of U.S. patent application Ser. No. 09/543,264 filed Apr. 5, 2000, now U.S. Pat. No. 6,944,501, issued Sep. 13, 2005, which are all hereby incorporated by reference in their entirety. All of the aforementioned applications and/or patents are assigned to the assignee of the present application.

FIELD OF THE INVENTION

This invention is to a neurostimulator, preferably implantable in the cranium, that is configured to treat epilepsy and other neurological disorders using certain stimulation strategies, particularly changing various pulse parameters during the imposition of a burst of those pulses. The invention also includes processes embodying those stimulation strategies.

BACKGROUND OF THE INVENTION

Epileptic seizures are characterized by excessive or abnormally synchronous neuronal activity. Neurologists recognize a wide variety of seizures. Partial onset seizures begin in one part of the brain; general onset seizures arise throughout the entire brain simultaneously. When partial onset seizures progress to involve much of the brain, they are said to have "secondarily generalized." Some seizures result in the loss of conscious awareness and are termed "complex" seizures. So-called "simple" seizures may involve other symptoms, but consciousness is unimpaired. Seizure symptoms may include sensory distortions, involuntary movements, or loss of muscle tone. The behavioral features of a seizure often reflect a function of the cortex where the abnormal electrical activity is found.

Physicians have been able to treat epilepsy by resecting certain brain areas by surgery and by medication. Brain surgery is irreversible, and is ineffective or is associated with neural morbidity in a sizable percentage of cases. Medication is the most prevalent treatment for epilepsy. It is effective in over half of patients, but in the reminder of the patients, the medication is either ineffective in controlling seizures, or the patients suffer from debilitating side effects. A more promising method of treating patients having epileptic seizures is by electrical stimulation of the brain.

Since the early 1970's, electrical brain stimulators have been used which provide more or less constant stimulation, the stimulation largely being unrelated to detected electrical activity.

Electrical stimulation of the nervous system has been used to suppress seizures. A device is described in Cooper et al. for stimulation of the cerebellum. See, "The Effect of Chronic Stimulation of Cerebellar Cortex on Epilepsy and Man," I. S. Cooper et al in *The Cerebellum, Epilepsy and Behavior*, Cooper, Riklan and Snyder Edition, Pleman Press, New York 1974. Others have utilized devices which stimulated the centro median nucleus of the thalamus. See, "Electrical Stimulation of the Centro Median Thalamic Nucleous in Control of Seizures: Long Term Studies." F. Valasco et al, *Epilepsia*, 36 (1): 63-71, 1995. Chaos Theory has been used to apply stimulation to a seizure focus in vitro to abort the seizure. See, S. Schiff et al, "Controlling Chaos in the Brain," *Nature*, Volume 370, Aug. 25, 1994.

As described in U.S. Pat. No. 6,016,449, an improved brain stimulator is implanted in the cranium and has leads terminating with electrodes in contact with brain tissue.

Conventional neurostimulators use fixed rate trains of either monophasic or biphasic electrical pulses of a fixed amplitude to stimulate neural tissue. Neurons in the immediate vicinity of the electrodes are induced to fire (i.e. are recruited) by the electrical pulses thereby modifying the natural electrical activity in the brain. During an epileptic event, there is abnormal synchronization of neural activity in the brain. The present invention improves upon the prior art by varying the timing, amplitude and/or duration of the pulses to more effectively disrupt the synchronized activity. Furthermore, the subject invention analyzes the effect on the brain of the electrical pulses, and decides how to modify the burst parameters in a subsequent burst to most effectively terminate the seizure.

Responsive stimulation, specifically electrical stimulation, that is applied to the brain, has not yet been used to treat patients in long-term studies. This is true even though there are algorithms suitable for detection of the onset of an epileptic seizure. For instance, Qu et al provide an algorithm said to recognize patterns of electrical activity similar to those developed while recording an actual epileptic seizure. See, Qu et al., "A Seizure Warning System for Long-Term Epilepsy Monitoring, *Neurology*," 1995; 45:2250-2254. Similarly, Osario, et al. have suggested an algorithm applied to signals from intracranial electrodes with good results. See Osario, et al. "A Method For Accurate Automated Real-Time Seizure Detection," *Epilepsia*, Vol. 35, supplement 4, 1995.

As used herein, "epileptiform activity" refers to the manifestation on an EEG (cortical, depth, or scalp) of abnormal brain activity whether associated with clinical manifestations or not. "Stimulation" or "electrical stimulation" means the application of an electric field or electric current to biological tissue.

The inventive device and related process:
1. have improved ability to terminate epileptiform activity.
2. are less likely to initiate epileptiform activity if stimulation is accidentally delivered during a normal EEG.
3. are less likely to generalize ongoing epileptiform activity.
4. are safer since the current density required to affect a larger amount of brain tissue is lower than that found in the prior art.

None of the cited documents describes the inventive procedures and devices described below.

BRIEF DESCRIPTION OF THE DRAWINGS

FIG. 6 depicts variously a representative EEG of epileptiform activity and a selection of burst initiations done according to the invention that represent various stages of delay from peaks detected as shown in FIGS. 5A-5C.

FIG. 8 is a depiction of one variation of the inventive neurostimulator having multiple electrodes.

DETAILED DESCRIPTION OF THE INVENTION

This invention recognizes the phenomenon that stimulation which precipitates epileptiform activity is promoting synchronized activity in the brain; stimulation intended to terminate epileptiform activity desynchronizes brain activity. Therefore different parameters for stimulation are better depending upon whether the burst is intended to provoke or terminate seizures.

This invention uses various parameters to optimize stimulation to desynchronize the brain activity to terminate epileptiform activity:

Pulse-to-Pulse Interval Variation

In one variation for treating epilepsy, the pulse-to-pulse interval within a burst is not fixed as in prior art devices. To better desynchronize neuronal activity, the pulse-to-pulse interval is varied as shown in FIG. 1. The pulse-to-pulse intervals are generally kept to a range of 3 to 300 msec, and may be varied randomly or changed in a systematic fashion, such as incrementing or decrementing the pulse to pulse interval within a burst. In addition to providing a better modality for terminating epileptiform activity, a burst with a varying pulse-to-pulse interval can be optimized to avoid inducing epileptiform activity, or generalizing a local seizure while maintaining high efficacy in terminating seizures. Once the electrodes are placed near the epileptogenic focus in the brain, the physician can use bursts of pulses both to initiate and to terminate epileptiform activity. By varying the burst parameters, it is possible to arrive at a parameter set that is effective at terminating epileptiform activity, but is ineffective at initiating it. For the purposes of this patent, a burst may be any number of pulses, typically in the range from 1 to 100.

Figure 1A:
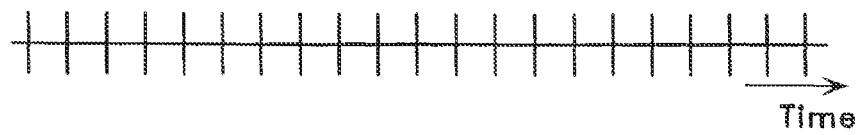
FIG. 1A shows constant pulse-to-pulse intervals in prior art burst.
Figure 1B:
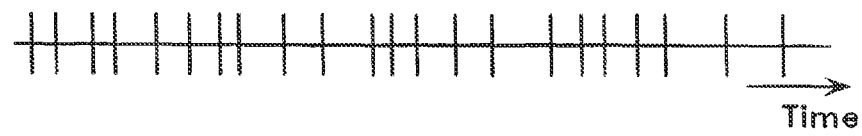
FIGS. 1B to 1E depict varying pulse-to-pulse intervals for a burst according to the inventive process.
Figure 1C:
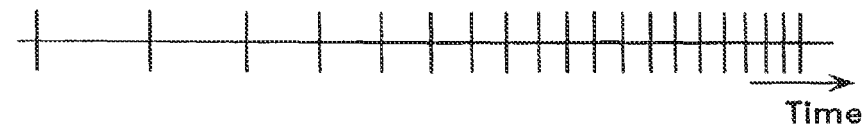
Figure 1D:
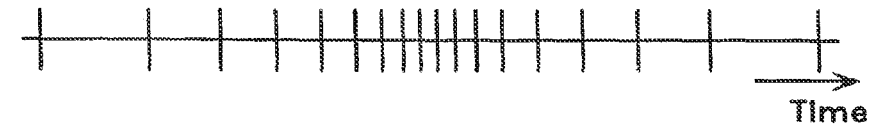
Figure 1E:
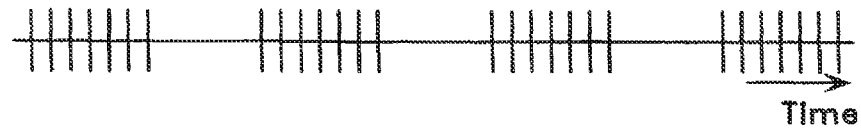

The examples shown in FIGS. 1A to 1E depict burst durations of approximately 400 msec for illustrative purposes. Burst durations of 10 msec to 2000 msec or even longer may all be effective in terminating epileptiform activity. FIG. 1A shows a prior art fixed rate burst with the pulse-to-pulse interval fixed at 20 msec. FIG. 1B shows a representative burst where the pulse-to-pulse interval is varied in a random, pseudo-random, or fractal fashion within the burst. FIG. 1C shows a burst where the pulse-to-pulse interval decrements within the burst. FIG. 1D shows a burst where the pulse-to-pulse interval first decrements and then increments within the burst. FIG. 1E shows a burst that is made up of shorter bursts. In the variation shown in FIG. 1E, the pulse sequence within the shorter bursts, the shorter burst durations, and the intervals between the shorter bursts may be varied as described with respect to FIGS. 1B to 1D. Additional burst patterns may be generated from the basic patterns described herein without departing from the scope of this invention.

Pulse Amplitude Variation

Another inventive method for desynchronizing brain activity and terminating epileptiform activity is by spatially desynchronizing activity in the vicinity of the stimulation electrode. To accomplish this, various individual pulse parameters within a burst are varied for at least a portion of the burst. Specifically, by varying the amplitude of the pulses, individual pulses may be tailored to directly depolarize different neural tissue. Lower amplitude pulses directly depolarize tissue in the immediate vicinity of the electrode; higher amplitude pulses directly depolarize tissue both near the electrode and at some distance from the electrode. By varying the amplitude of the pulses within a burst, local tissue is depolarized at a higher rate than tissue somewhat distant from the electrode. The spatial heterogeneity of the timing of depolarization around the electrode is more effective in desynchronizing brain activity than prior art pulse regimes.

Figure 2A:
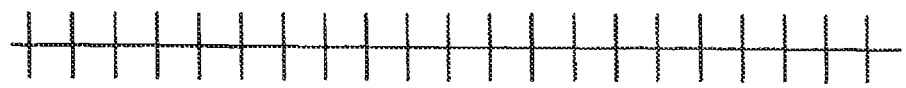
FIG. 2A shows a prior art burst having a constant pulse amplitude.
Figure 2B:
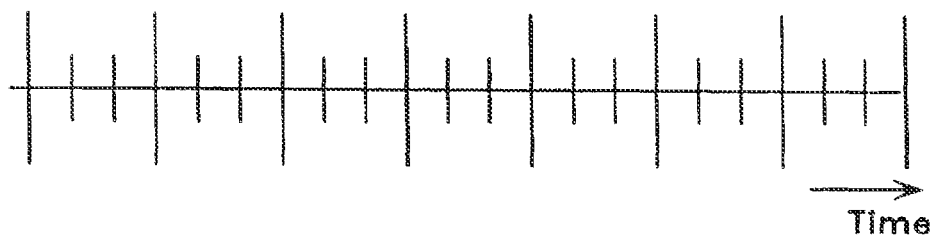
FIGS. 2B and 2C depict varying pulse amplitudes for a burst according to the inventive process.
Figure 2C:
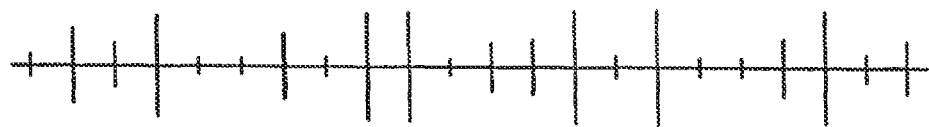

In FIG. 2A to 2C, the fixed rate bursts are depicted with durations of approximately 400 msec for illustrative purposes only. FIG. 2A shows an example of a prior art, fixed amplitude burst. FIG. 2B shows a burst having a systematic variation of pulse amplitude within the burst. FIG. 2C shows a burst where the pulse amplitude within the burst varies in a random, pseudo-random, or fractal fashion.

Hyperpolarizing Prepulse

Figure 3A:
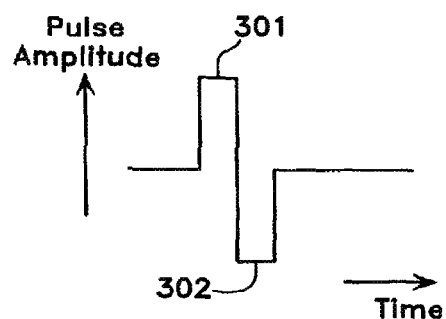
FIG. 3A shows a typical prior art pulse.
Figure 3B:
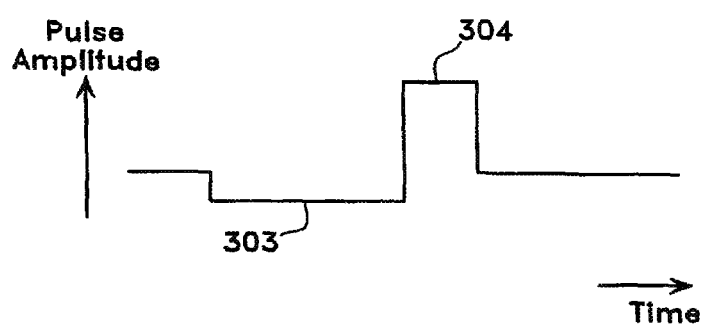
FIG. 3B shows a pulse with a hyperpolarizing prepulse.

A variation of the inventive technique is to include a hyperpolarizing prepulse to render tissue near the electrode less sensitive than tissue at some distance from the electrode. This allows more independent control of the sequence of depolarization of tissue near and more distal to the electrode. FIG. 3A shows a typical prior art pulse having a stimulating phase 301 and a charge balance phase 302 of equal duration. Typical phase durations vary from 40 to 500 microseconds. FIG. 3B shows a pulse having a hyperpolarizing prephase 303 followed by a stimulating phase 304. The prephase 303 is typically of low amplitude and longer duration, and would not stimulate tissue effectively if used on its own. The stimulating phase 304 is of higher amplitude and its duration may be adjusted to charge balance the hyperpolarizing prephase 304. The pulse described in FIG. 3B maybe used selectively or throughout the stimulation strategies discussed in conjunction with the inventive variations found above.

Pulse Width Variation

In addition to varying the pulse amplitude, it is advantageous also to vary the pulse width of individual pulses within a burst. Shorter pulses (on the order of 50 to 150 microseconds) tend to directly depolarize smaller diameter nerve cells. Longer pulses (100 to 500 microseconds) depolarize larger diameter nerve cells. By varying the pulse width of the pulses within a burst, it is possible to preferentially depolarize larger nerves with some of the pulses and smaller nerves with other pulses. The result is a greater spatial variation of the distribution of stimulated nerves on a pulse by pulse basis which results in greater efficacy in desynchronizing brain activity thereby terminating epileptiform activity.

Figure 4A:
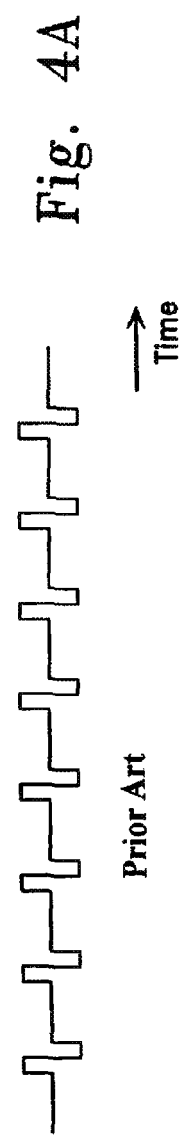
FIG. 4A shows a prior art burst having constant pulse widths.
Figure 4B:
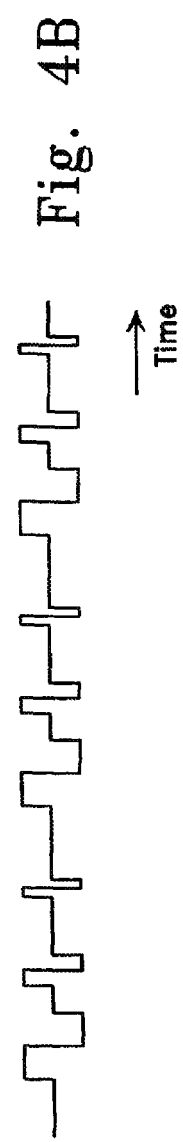
FIGS. 4B and 4C depict varying pulse widths for a burst according to the inventive process.
Figure 4C:
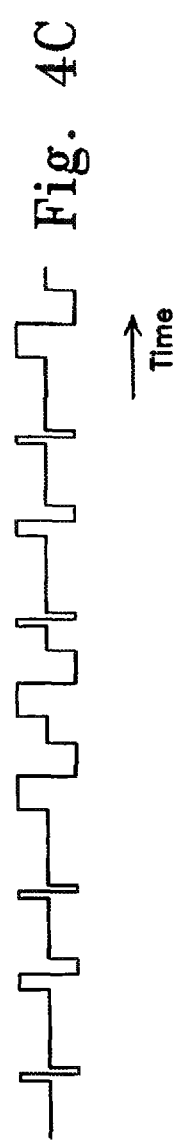

In FIGS. 4A to 4C, the number of pulses within the bursts is fewer than in previous examples, and the width of the pulses within the bursts is exaggerated for clarity. FIG. 4A shows a typical prior art burst where the pulse widths of the pulses within the burst are all the same. FIG. 4B is an example of a burst where the pulse widths are varied in systematic fashion. FIG. 4C is an example of a burst where the pulse widths are varied in a random, pseudo-random or fractal fashion.

Since the tissue disposed near an electrode may have highly variable anatomy, it is anticipated that all of the parameters described above with regard to the Figures (e.g., pulse to pulse interval, pulse amplitude, the use of hyperpolarizing pulses, and pulse width) may be varied alone or in combination to optimize the ability of a burst to terminate epileptiform activity in the brain while improving the safety of the burst by reducing the likelihood of inducing epileptiform activity or generalizing such pre-existing activity.

EEG-Based Stimulation—Pulse-to Pulse Interval

In addition to producing bursts that contain intervals that are set in absolute time increments, this invention provides the improvement of setting pulse-to-pulse interval based upon the detected interval of the epileptiform activity as sensed on the electrodes in contact with the brain. In this mode of operation, the rate of the sensed epileptiform activity is detected and measured. The rate of the detected activity may be used to determine specific pulse-to-pulse intervals or average pulse-to-pulse intervals of the burst used to terminate the epileptiform activity.

Figure 5A:
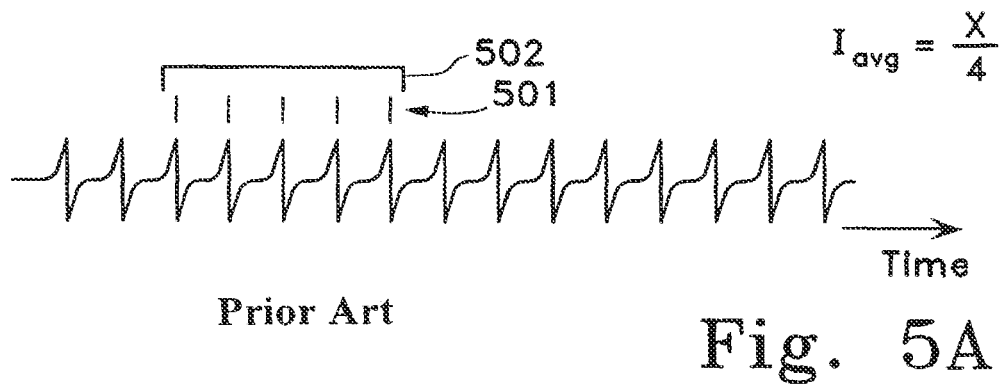
FIGS. 5A, 5B, and 5C depict epileptiform activity in the brain.
Figure 5B:
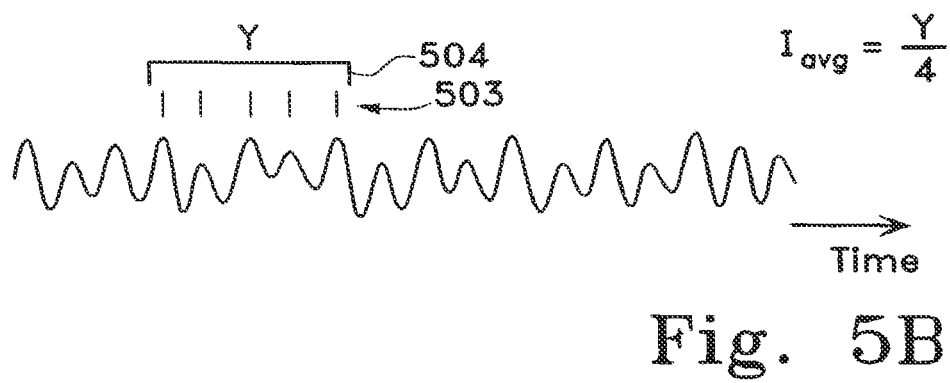
Figure 5C:
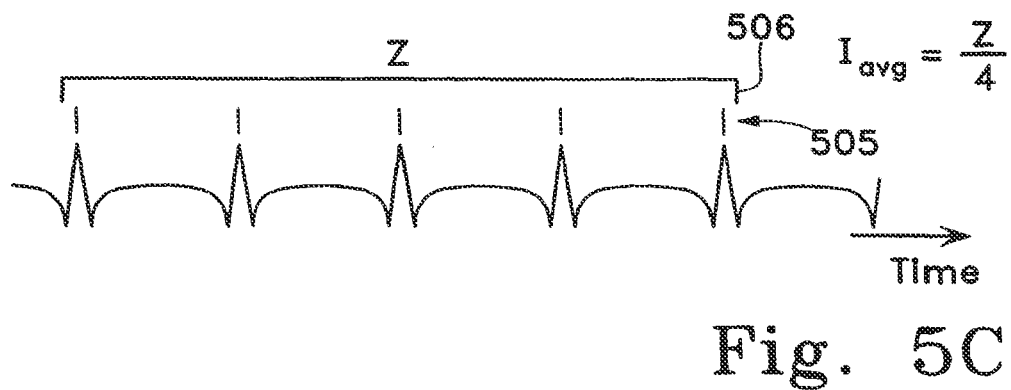

FIG. 5A to 5C illustrate a method for generating a burst where some or all of the pulse-to-pulse intervals are based upon the rate of the epileptiform activity. FIGS. 5A, 5B, and 5C show typical examples of epileptiform activity detected from electrodes in contact with the cortex near the epileptogenic region of a brain. The first step is to determine the rate or average rate of the epileptiform activity. By detecting the peaks of the epileptiform activity, and counting (for example) four intervals, and dividing the result by four, the average interval, $I_{avg}$, may be determined. Peak detection and interval measurement is well known in the art of automated EEG analysis. See, for instance, "Automatic Detection of Seizures and Spikes" Jean Gotman, Journal of Clinical Neurophysiology, 16(2):13-140, 1999 and U.S. patent application Ser. No. 09/517,797, filed Mar. 2, 2000, entitled "Neurological Event Detection Using Processed Display Channel Based Algorithms and Devices Incorporating These Procedures", the entirety of which are incorporated by reference.

Peak markers 501, 503, and 505 in FIGS. 5A, 5B, and 5C respectively delineate four intervals of each of the epileptiform examples. The measurements X, Y, and Z shown by 502, 504 and 506 in FIGS. 5A, 5B and 5C respectively are divided by four to give the $I_{avg}$ in each case. It may be desirable to use more or less intervals in calculating the interval average, or the mode or some other mathematical means may be used without departing from the intention of this invention.

Once the $I_{avg}$ has been determined, it may be used in my inventive process to set pulse-to-pulse intervals within a burst. For example in FIG. 1A, the pulse-to-pulse interval in the fixed rate burst may be determined by taking a percentage of the measured $I_{avg}$. The following table of derived pulse-to-pulse intervals for a burst provides a number of calculated percentages, the use of which will be apparent just below:

| Measured $I_{avg}$ (msec) | | 60 | 80 | 120 |
|---|---|---|---|---|
| Percent | 10% | 6 | 8 | 12 |
| | 20% | 12 | 16 | 24 |
| | 30% | 18 | 24 | 36 |

As can be seen, for a given programmed setting of percentage, the pulse-to-pulse interval of the burst varies to accommodate different epileptiform waveforms. This provides an advantage over prior art fixed rate intervals in terminating epileptiform activity.

To apply the same principle to the burst of 1B, the average pulse-to-pulse interval may then be set to be equal to a percentage of the measured $I_{avg}$. For FIGS. 1C and 1D, the initial interval may be set equal to or set to a percentage of the measured $I_{avg}$. Subsequent intervals may then be calculated by adding or subtracting a fixed value or percentage from the previous interval. The pulse-to-pulse intervals shown in FIG. 1E may calculated in the same manner as those of the previous examples.

The range of percentages used may be from 5% to 300% of the measured $I_{avg}$ depending on the application, and the patient's condition.

EEG-Based Stimulation—Synchronization/Delay

To further improve the efficacy of a burst in terminating epileptiform activity, the subject invention also provides for synchronization of the burst with the EEG (FIG. 6). To do this, a timing signal is generated off of the sensed EEG. A delay that varies from 0 to 100% of the detected EEG interval is initiated from the timing signal and is used to trigger the start of the burst. Graph 180 shows a representative EEG of epileptiform activity. Stimulation 182 shows a burst delivered with a 0% delay, that is simultaneous with a spike on the EEG. Stimulation 184 shows a representative burst having a 50% delay; and Stimulation 186 depicts a burst having a 75% delay. The synchronization technique described with regard to FIG. 6 may be used in conjunction with the adaptive pulse-to-pulse interval as described in conjunction with FIGS. 5A to 5C in that a minimal number of pulses may be used in a burst, in some cases as few as one, but more typically three or four. By minimizing the number of pulses, a burst which is effective in terminating epileptiform activity is safer as it is less likely to provoke a seizure if accidentally applied.

A further method of synchronizing a burst is to trigger the first pulse of the burst selectively on a positive peak, a negative peak, or some other feature of the EEG signal. The detected EEG is preferentially from an electrode near or on the epileptogenic focus, but different features may be used to optimize the synchronization of the burst depending upon where the electrode is relative to the epileptogenic activity in the brain, and the patient's condition.

EEG-Based Stimulation—Detection and Repetition

After the burst is delivered, the EEG is re-examined, and if the epileptiform activity was not terminated, a subsequent burst is delivered. The subsequent burst may have the same parameters as the first burst, may re-adapt to the changing EEG rate, or may have new parameters to more aggressively attempt to terminate the epileptiform activity (e.g. higher rate, more pulses, higher output, or modified pulse-to-pulse intervals).

Spatially-Determined Stimulation

Figure 7A:
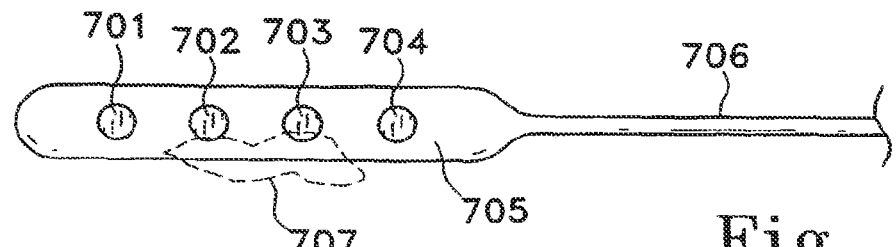
FIGS. 7A to 7E depict examples of bursts with varying pulse parameters as might be applied to the FIG. 7A device.
Figure 7B:
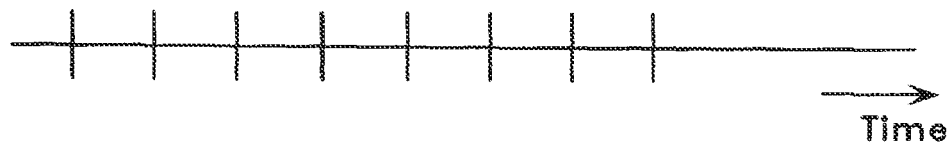
Figure 7C:
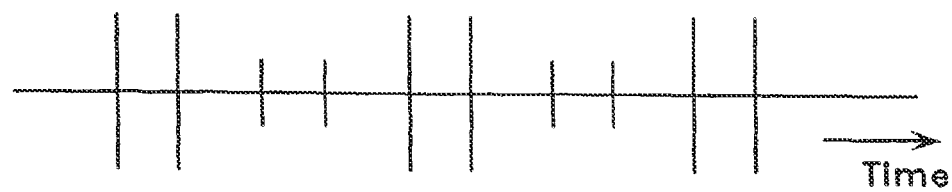
Figure 7D:
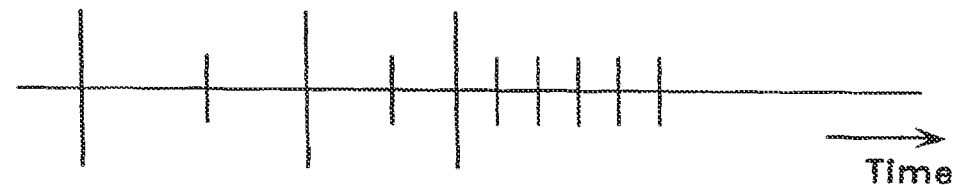
Figure 7E:
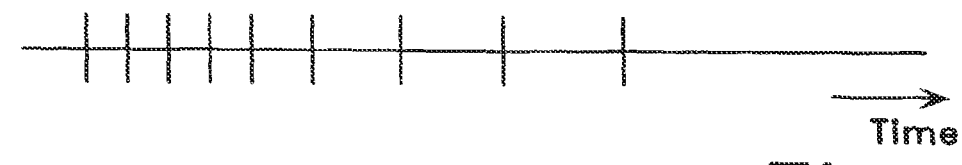

One important aspect of this invention is the potential use of multiple brain contact electrodes to provide therapy. One embodiment of a device especially suitable for practicing certain variations of the inventive process is shown in FIG. 7A. The FIG. 7A includes multiple electrodes 701, 702, 703, and 704, to enhance the ability of electrical stimulation to desynchronize brain activity to terminate epileptiform activity. Although the same burst may be delivered from a multiplicity of electrodes in the vicinity of the epileptogenic focus, it is preferable to provide bursts having different parameters, particularly pulse-to-pulse timing, to achieve a greater degree of spatial heterogeneity of neural activity and thereby most effectively desynchronize brain activity. This method for terminating epileptiform activity provides additional benefits in that lower current densities at the electrodes may be used to affect a larger amount of brain tissue than if a single electrode were used. Lower current densities are associated with fewer histological changes in the vicinity of the stimulating electrodes. Furthermore, the use of different burst parameters and/or lower current densities from a number of electrodes is less likely to initiate epileptiform activity or generalize ongoing epileptiform activity.

FIG. 7A depicts a representative electrode assembly placed under the dura mater on the brain, and viewed from above. There are four electrodes 701, 702, 703 and 704 in an insulated electrode backing 705 that prevents current flow back to the dura mater. Current flow back to the dura matter is often uncomfortable for the patient. The electrodes are electrically connected to the neurostimulator (not shown) by wires enclosed in the lead body 706. The epileptogenic region 707 is outlined for clarity, but is generally not visually apparent. To achieve spatial heterogeneity of electrical stimulation to most optimally desynchronize neuronal activity, the strategies described in this patent may be applied to all the electrodes 701-704 together or separately. FIGS. 7B, 7C, 7D, and 7E show an example of separate burst parameters being applied to electrodes 701, 702, 703 and 704 respectively to desynchronize neuronal activity in a wide area of brain tissue near the epileptogenic focus.

Implantable Neurostimulator

The inventive device includes a neurostimulator central unit and at least one electrode. The neurostimulator central unit includes the necessary circuitry, e.g., A/D converters, filters, central processing unit(s), digital processing circuits, blanking circuits, power supplies, batteries, signal generators, etc., and programming configured and adapted to perform the inventive steps listed above. Specifically the neurostimulator central unit (800) desirably is as shown in FIG. 8 and is shaped in such a way that it conforms to the shape of the skull, although it need not be so. The neurostimulator central unit should at least contain an electrical stimulation source and preferably devices for detecting epileptiform activity and for initiating and for varying the responsive electrical stimulation as described above. The neurostimulator assembly should also include at least a first brain electrical activity sensor (802) and a responsive electrical neurostimulator electrode (804), preferably in the form shown in FIG. 7A. The various necessary connectors, leads, and supporting components are also included.

A highly desirable aspect of the inventive device is the use of multiple brain electrodes to provide therapy. The measuring electrodes are preferable in contact with the brain, but, as discussed above, may be scalp electrodes or within the brain tissue. Multiple electrodes enhance the ability of electrical stimulation to desynchronize brain activity in terminating epileptiform activity. Although the same burst may be delivered from a multiplicity of electrodes in the vicinity of the epileptogenic focus, as noted above, preferable to introduce bursts having different signal parameters, particularly pulse-to-pulse timing, to the brain to achieve a greater degree of spatial heterogeneity of neural activity and most effectively desynchronize brain activity.

The application of multiple electrodes to different parts or regions of the brain also provide a way to treat epilepsy having more than one focus. Electrodes are placed on or near the various epileptogenic foci. The inventive neurostimulator may sense and stimulate independently from each electrode. Optional amplifier blanking eliminates cross talk, and logical flow in the device's software keeps the device from erroneously detecting its own output as epileptiform activity.

This inventive device may utilize independently actuatable, spatially separated electrodes so that those epilepsies having many epileptogenic foci or for which the focus is so diffuse the seizure arises from a large portion of the brain, may be treated. In such a case, it is desirable to place one electrode deep in the brain, preferably in the area of the hippocampus. Additional electrodes may be placed on the surface of the cortex. When epileptiform activity is detected, the device stimulates from the hippocampal region to take advantage of the large number of neural pathways emanating from that area into the cortex. Electrodes on the cortex provide additional electrical access to the brain allowing electrical stimulation to terminate epileptiform activity having a greater spatial extent.

Although preferred embodiments of the invention have been described herein, it will be recognized that a variety of changes and modifications can be made without departing from the spirit of the invention as found in the appended claims.

What I claim is:

1. A method for treating an abnormal neurological condition comprising:
   generating at least one electrical burst to deliver to brain tissue as a therapy for an abnormal neurological condition, each electrical burst characterized by burst parameters and a timing parameter that determines when each electrical burst will be applied;
   sensing an electrical signal from brain tissue prior to generating each electrical burst, the sensed electrical signal representative of electrical activity of the brain;
   analyzing the sensed signal to determine whether it represents an abnormal neurological condition and, if so, determining an onset time for the abnormal neurological condition and an interval that characterizes the sensed electrical signal;
   establishing a value of the timing parameter so that each electrical burst will be triggered for application to brain tissue after the onset time and at a time corresponding to a range of between 5% and about 100% of the determined interval;
   triggering each electrical burst according to the onset time and the timing parameter; and
   applying each electrical burst according to the burst parameters.

2. The method of claim 1 wherein:
   analyzing the sensed signal to determine whether it represents an abnormal neurological condition further comprises analyzing the sensed signal for epileptiform activity; and
   triggering each electrical burst according to the onset time and the timing parameter further comprises triggering each electrical burst in response to the epileptiform activity.

3. The method of claim 2 wherein generating at least one electrical burst includes generating at least one electrical burst with a plurality of pulses, and the burst parameters characterizing each electrical burst includes a pulse-to-pulse interval; and
   further comprising establishing a set of values of the pulse-to-pulse interval so that the pulse-to-pulse interval is a function of the determined interval.

4. The method of claim 2 wherein determining an interval that characterizes the sensed electrical signal further comprises:
   detecting an epileptiform activity rate by:
      counting a number of peaks that characterize the sensed electrical signal;
      measuring a time over which the number of peaks occur;
      calculating an average interval by dividing the measured time by the number of peaks; and
      determining the interval to be the average interval.

5. The method of claim 4 wherein each electrical burst comprises a plurality of pulses and the burst parameters include a pulse-to-pulse interval; and further comprising establishing a set of values of the pulse-to-pulse interval so that the pulse-to-pulse interval is a function of the determined interval.

6. The method of claim 5 wherein the pulse-to-pulse interval is a function of the detected epileptiform activity rate.

7. The method of claim 6 wherein the set of values of pulse-to-pulse interval comprises one value corresponding to a time between each pair of pulses within each electrical burst.

8. The method of claim 6 wherein the set of values of the pulse-to-pulse interval comprise at least two different values and each value corresponds to a time between each pair of pulses within each electrical burst.

9. The method of claim 8 wherein one of the values of the set of values of the pulse-to-pulse interval corresponds to the determined interval and one of the values of the pulse-to-pulse interval corresponds to the addition of a fixed amount to the determined interval.

10. The method of claim 8 wherein one of the values of the set of values of the pulse-to-pulse interval corresponds to the determined interval and one of the values of the pulse-to-pulse interval corresponds to the addition of a percentage to the determined interval wherein the percentage is a percentage of the determined interval.

11. The method of claim 8 wherein one of the values of the set of values of the pulse-to-pulse interval corresponds to the determined interval and one of the values of the pulse-to-pulse interval corresponds to the subtraction of a fixed amount to the determined interval.

12. The method of claim 8 wherein one of the values of the set of values of the pulse-to-pulse interval corresponds to the determined interval and one of the values of the pulse-to-pulse interval corresponds to the subtraction of a percentage to the determined interval wherein the percentage is a percentage of the determined interval.

13. The method of claim 1 wherein the burst parameters characterizing each electrical burst include a prepulse parameter a value of which determines whether each electrical burst will have any hyperpolarizing prepulses; and, if the prepulse parameter value determines that each electrical burst will have any hyperpolarizing prepulses, generating each electrical burst so that the hyperpolarizing prepulses are applied.

14. The method of claim 1 wherein each electrical burst comprises a plurality of pulses and the burst parameters characterizing each electrical burst include an amplitude parameter a value of which determines what the amplitude of each pulse will be and further comprising applying each electrical burst while varying the value of the amplitude parameter.

15. The method claim 1 wherein each electrical burst comprises a plurality of pulses and the burst parameters characterizing each electrical burst include a pulse width parameter a value of which determines what the pulse width of each pulse will be and further comprising applying each electrical burst while varying the value of the pulse width parameter.

16. A method of delaying application of a burst of electrical stimulation to brain tissue after the onset of an abnormal neurological condition based on a detected interval in an electrographic signal sensed from a patient's brain comprising:

sensing an electrographic signal and analyzing the sensed signal to identify peaks and, if a recurring pattern of peaks is identified, determining an onset time of the recurring pattern and a interval corresponding to a time between two peaks or to an average time between peaks; and after the onset time, applying a burst of electrical stimulation to brain tissue according to a delay that is a function of the interval.

17. The method of claim 16 wherein the burst is applied at a time after the onset time that is a percentage of the interval in the range of greater than 0% and up to 100% of the interval.

18. The method of claim 16 wherein the recurring pattern of peaks represents epileptiform activity.

19. The method of claim 18 further comprising, if epileptiform activity continues to be sensed, repeating the sensing and applying steps unless the epileptiform activity no longer continues to be sensed or a maximum limit for stimulation has been exceeded.

20. A method of synchronizing application of a burst of electrical stimulation to brain tissue after the onset of an abnormal neurological condition identified in an electrographic signal sensed from a patient's brain comprising:

sensing an electrographic signal and analyzing the sensed signal to identify peaks and, if a recurring pattern of peaks is identified, determining an onset time of the recurring pattern; and after the onset time, applying a burst of electrical stimulation to brain tissue so that the start of the burst is expected to occur on a peak in the recurring pattern of the electrographic signal.

* * * * *